(12) United States Patent
Munn

(10) Patent No.: US 10,307,504 B2
(45) Date of Patent: Jun. 4, 2019

(54) DISINFECTING APPARATUS DEVICE

(71) Applicant: STERILUMEN, INC., Tarrytown, NY (US)

(72) Inventor: Max Munn, Tarrytown, NY (US)

(73) Assignee: SteriLumen, Inc., Tarrytown, NY (US)

( * ) Notice: Subject to any disclaimer, the term of this patent is extended or adjusted under 35 U.S.C. 154(b) by 0 days.

(21) Appl. No.: 15/707,669

(22) Filed: Sep. 18, 2017

(65) Prior Publication Data

US 2019/0083672 A1    Mar. 21, 2019

(51) Int. Cl.
*A61L 2/24* (2006.01)
*A61L 9/20* (2006.01)
*A61L 2/10* (2006.01)

(52) U.S. Cl.
CPC ..................... *A61L 9/20* (2013.01); *A61L 2/10* (2013.01); *A61L 2/24* (2013.01); *A61L 2202/11* (2013.01); *A61L 2202/14* (2013.01); *A61L 2209/12* (2013.01)

(58) Field of Classification Search
CPC .................. A61L 9/20; A61L 2/10; A61L 2/24
See application file for complete search history.

(56) References Cited

U.S. PATENT DOCUMENTS

| | | | |
|---|---|---|---|
| 6,773,682 B1 | 8/2004 | Benda | |
| 8,662,705 B2 | 3/2014 | Roberts | |
| 8,900,518 B2 | 12/2014 | Seck | |
| 9,028,084 B2 * | 5/2015 | Maeng | F25D 17/042 362/92 |
| 9,308,289 B2 | 4/2016 | Graff et al. | |
| 9,480,768 B2 | 11/2016 | Krosney et al. | |
| 9,724,442 B1 | 8/2017 | Munn | |
| 9,974,875 B2 * | 5/2018 | Davis | A61L 2/10 |
| 2002/0098127 A1 | 7/2002 | Bollini | |
| 2007/0053188 A1 | 3/2007 | New et al. | |
| 2009/0291029 A1 | 11/2009 | Ogasawara | |

(Continued)

FOREIGN PATENT DOCUMENTS

| | | |
|---|---|---|
| CN | 202526007 | 11/2012 |
| CN | 202629828 | 12/2012 |

(Continued)

OTHER PUBLICATIONS

Official Publication of the International Ultra Violet Association, IUV ANews http://www.luva.org/Publications.

*Primary Examiner* — Sean E Conley
(74) *Attorney, Agent, or Firm* — Myron Greenspan; Lackenbach Siegel LLP

(57) ABSTRACT

A disinfecting apparatus may include a shelf securable to a wall; a mount configured to secure the shelf to the wall; at least one UV light source coupled to the shelf, the UV light being configured to sanitize air and surfaces in close proximity to the UV light source; and a programmable controller being operatively coupled to the motion detector, the controller being configured to cause cause at least one of energization and de-energization of the UV light source upon a predetermined event. A method of safely disinfecting or sterilizing air and surfaces may include the apparatus and may further provide UV light in the range of 250-290 nm and interruption of the generation of UV light in response to the predetermined event.

9 Claims, 4 Drawing Sheets

(56) References Cited

U.S. PATENT DOCUMENTS

| | | | |
|---|---|---|---|
| 2010/0032589 A1* | 2/2010 | Leben | A61L 2/10 |
| | | | 250/504 R |
| 2012/0051030 A1* | 3/2012 | Johnson | F25D 17/042 |
| | | | 362/92 |
| 2012/0199005 A1 | 8/2012 | Koji et al. | |
| 2015/0360606 A1 | 12/2015 | Thompson et al. | |
| 2017/0007736 A1 | 1/2017 | Engelhard | |
| 2017/0049915 A1* | 2/2017 | Brais | H05B 37/0227 |
| 2017/0073722 A1* | 3/2017 | Kanhye | C12Q 1/04 |
| 2017/0340761 A1* | 11/2017 | Shur | A61L 2/10 |

FOREIGN PATENT DOCUMENTS

| | | |
|---|---|---|
| CN | 203633880 | 6/2014 |
| CN | 205561091 | 9/2016 |
| KR | 20120133286 | 12/2012 |

* cited by examiner

DISINFECTING APPARATUS DEVICE

BACKGROUND

Technical Field

This disclosure generally relates to a disinfecting apparatus, and more specifically, to a hazard-free shelf that disinfects and purifies air by exposing pathogens to a source of ultraviolet (UV) light within the range of 250-290 nm for use in medical and other facilities.

Description of the Related Art

Health care-acquired infections (HAIs) in hospitals, assisted living facilities, etc., are serious health problems. It has been estimated that HAIs cause or contribute in excess of 99,000 deaths annually in the United States. The Center for Disease Control (CDC) reports 1 in 25 patients will contract at least one infection during their stay. Various bacteria become immune or resistant to disinfectants applied to surfaces in hospitals and other medical facilities, these bacterias commonly cause what are being referred to as "staph" infections because they are resistant to many chemical disinfectants used to clean counter tops and other surfaces in hospital rooms and the like. The general problem is discussed, for example, in the Official Publication of the International Ultra Violet Association, IUVANews. http://www.iuva.org/Publications. These infections are considered preventable. In 2011 the federal government stopped reimbursing hospitals for the care of patient that acquired an infection during their stay. Additional penalties for high infection rates have since been added that are in some situations as much as 40% of the overall revenue.

One of the hurdles to success are multi drug resistant organisms (MDRO) that are resistance to standard disinfection products and practices. This has opened the door for new technologies such as UV-C (UV).

Each year over one million patients contract diseases unrelated to their initial stay at a hospital. Approximately 100,000 Americans die each year for this reason. The cost, both emotionally and financially is staggering and difficult to calculate.

The greatest concentration of pathogens within a hospital room likely occurs at the surface in the area surrounding the sink in the bathroom. Specifically, the faucet and the handles and the surface between these controls, and the back splash behind the sink, including the wall surface just above the sink is the most infected area in the typical hospital room.

Various UV devices have been proposed to reduce infectious pathogens. For example, bathrooms in airplanes have started to use UV LED strips to reduce pathogens while in flight. Other facilities are being outfitted with various devices to expose pathogens to UV light sources. However, UV light sources have generally been independent or stand alone devices that are specifically designed for intermittent applications and for that purpose only.

SUMMARY OF THE INVENTION

In an embodiment of the present disclosure, a disinfecting apparatus may include: a shelf securable to a wall; a mount configured to secure the shelf to the wall; at least one UV light source coupled to the shelf, the UV light being configured to sanitize air and surfaces in close proximity to the UV light source; and a programmable controller being operatively coupled to the motion detector, the controller being configured to cause cause energization and deenergization of the UV light source upon predetermined events. The mounting means may include a vertical surface configured to contact the wall and be fastened thereto. The source of UV light source may include at least one of an UV LED light, a mercury tube, and a xenon UV tubes. The source of UV light may include a plurality of UV-generating LEDs. The source of UV light source may generate ultraviolet radiation within the range of 250-290 nm. The apparatus may further include a heat sink to prevent said source of UV light from reaching excessive temperatures. In addition, the UV light source may include a plurality of strips of LEDs. The strips of LEDs may be generally parallel to one another and disposed along a length of the shelf.

In an embodiment of the present disclosure, a method of safely disinfecting or sterilizing air and surfaces, including: mounting a disinfecting apparatus to a wall. The apparatus may include: a shelf securable to the wall; a mount configured to secure the shelf to the wall; at least one UV light source coupled to the shelf, the UV light being configured to sanitize air and surfaces in close proximity to the UV light source; a control means being configured to cause cause energization and de-energization of the UV light source upon a predetermined event; providing UV light in the range of 250-290 nm; and interrupting the generation of UV light in response to the predetermined event, which may include at least one of detection of motion in the proximity of the mirror and a duration of time. The control means may include a motion detector and/or a programmable controller.

The source of UV light source may include at least one of an UV LED light, a mercury tube, and a xenon UV tubes. The UV light source may include one or more strips of LEDs, which may be oriented parallel to one another and disposed along a length of the shelf. The apparatus may further include a motion detector. The apparatus may further include a heat sink to prevent said source of UV light from reaching excessive temperatures.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention. For a more complete understanding of the present invention, reference is now made to the following drawings in which:

DETAILED DESCRIPTION OF THE PREFERRED EMBODIMENTS

Figure 1:
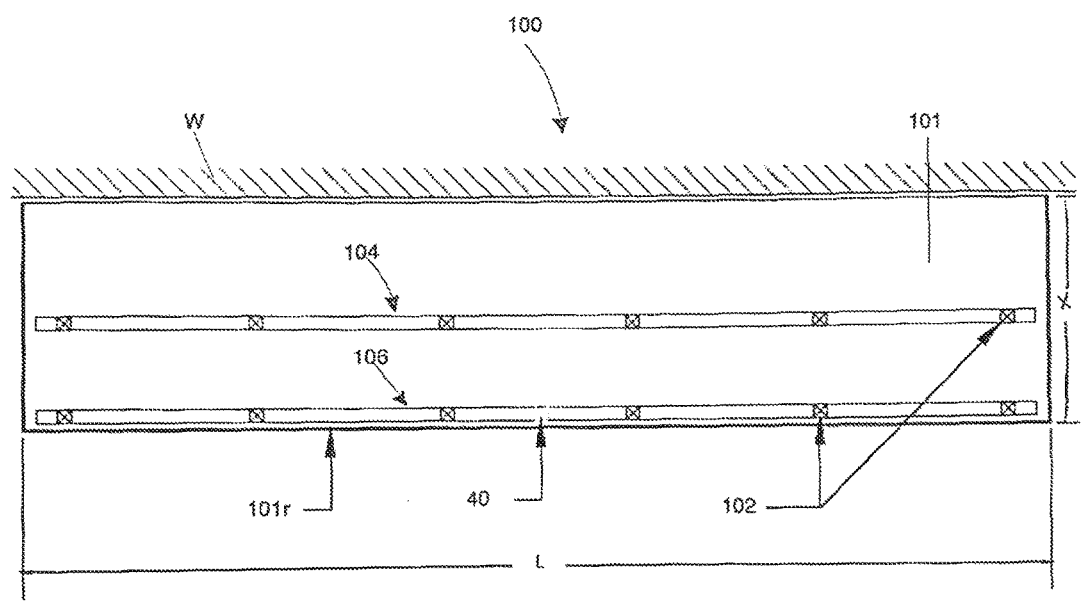
FIG. 1 is a bottom view of an embodiment of a disinfecting apparatus in accordance with the present disclosure.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

The 20 or so most prevalent and dangerous pathogens, in the hospital and which congregate in the above area can be very significantly reduced when exposed to ultra-violet waves in the range of 270-280 nanometers in length, a fact that is now well documented. The UV diodes that generate this particular wave length [referred to as UVC waves] have in the last few years become commercially available. The United States represents 25-35 percent of the current international hospital market. Additional markets include: (a) washrooms or bathrooms in assisted living restrooms; (b) commercial facilities such as offices and restaurants; and (c) the residential market or the hotel market.

The present application provides an aesthetically acceptable and easy to install apparatus incorporating such UV diodes to safely provide 99.99% destruction of pathogens when used for approximately 45 minutes to 2 hours, 6 times over a 24-hour period. Further, the applicant of the subject application has filed patent applications related to U.V. disinfection including U.S. patent application Ser. No. 15/601,607, filed May 22, 2017 for HAZARD-FREE DISINFECTING VANITY MIRRORS, which is a continuation-in-part of U.S. patent application Ser. No. 15/418,231, filed Jan. 27, 2017 for a DISINFECTING VANITY MIRROR, which is now U.S. Pat. No. 9,724,442, the entire contents of each of which are hereby incorporated by reference in their entireties.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

A disinfecting apparatus 100 in accordance with the present disclosure will now be described with reference to FIGS. 1-4.

As shown in FIG. 1, the disinfecting apparatus 100 may include a shelf 101 that has been secured to a wall W. The shelf 101 may have a length L and a width X, and may include at least one UV emitting light source 102, which may be secured to an underside of the shelf 101. The light source 102 may be configured to emit light of a suitable wavelength to have a disinfecting effect to kill pathogens that may be present at or near the light source 102. The shelf 101 may alternatively be an existing shelf with which the light source 102 may be integrated.

The light source 102 may emit light within the range of 250-290 nm, and preferably within the range of 270-280 nm. As indicated in the IUVANews publication ultraviolet radiation is defined most broadly as consisting of radiation within the range of 10-400 nm. However, most effective for germicidal applications is the short wave ultraviolet light normally designated as UV-C. UV-C includes wavelengths of 250-290 nm, although 270-280 nm are most effective for sanitizing or sterilizing airborne pathogens. UV light in that range is most efficiently absorbed by DNA, with maximum absorption being at approximately 270 nm. UV-C has been used for air purification, sterilization and disinfection. High intensity UV at 270 nm radiation can destroy DNA in living micro organisms. The effectiveness of the UV radiation is directly related to intensity and exposure time.

Advantageously, the disinfecting apparatus 100 is an inexpensive and reliable way of exposing air contaminated with pathogens to UV-C light on an ongoing or continuing basis when energized to increase the effectiveness of the sanitization and decontamination of microorganisms which may be airborne or on surfaces at or near the UV light source 102. The present disinfecting apparatus 100 is convenient, inexpensive and an effective way to neutralize micro-organisms and pathogens by exposure to the UV light emitted by UV light source 102.

As will be discussed, the disinfecting apparatus 100 while being configured to treat air and/or surfaces near the UV light source 102 is also configured to minimize harmful exposures to individuals who may be near the light source 102, for example, by turning off the light source 102 upon the approach of such individuals and by placing the light source 102 in a location where an individual is less prone to be exposed to the light, for example, by minimizing the exposure to the user's eyes or skin.

Preferably, the UV light source 102 is an LED light strip, which ha a considerably longer lifespan than other sources of light such as mercury lamps or bulbs. However, it is to be understood that the light source 102 may be any light source including UV mercury lamps or bulbs or fluorescent tubes, xenon lamps, or any lamp with a UV wave generating component, waves, or light.

Figure 2:
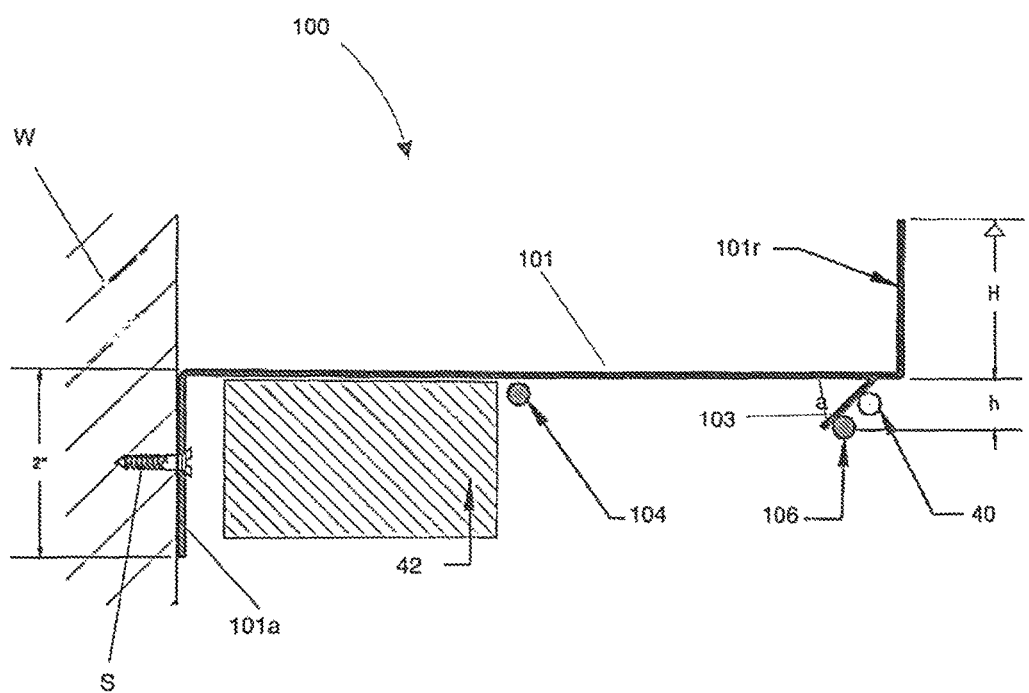
FIG. 2 is a side cross-sectional view of the disinfecting apparatus of FIG. 1 taken along line 2-2.

Moreover, as shown in FIG. 2, an angle 103, which may be formed from aluminum or another suitable material, may be mounted on a lower edge of the shelf 101 and may serve as a heat sink to prevent excessive heat from developing in the UV light source 102, thereby promoting reliability and longevity of the UV light source 102 by inhibiting excessive heat buildup. As shown in FIG. 2, the angle 103 may define an angle a relative to the shelf and may extend downward from the shelf by a distance h.

As shown best in FIG. 1, the disinfecting apparatus 100 may include a first light strip 104 and a second light strip 106. Each of the light strips 104, 106 may include a plurality of the light sources 102 that are configured to emit ultraviolet (UV) light. The first and second light strips 104, 106 may be generally rectangular in shape and include a plurality of the light sources 102 along their lengths. The first and second strips 104, 106 may be oriented substantially parallel to one another along the length L of the shelf 101, and spaced apart from one another along the width X of the shelf 101.

The shelf 101 may include a rail or lip 101r disposed at or around the periphery of the shelf 101 such that items placed thereon are inhibited from falling off. As shown in FIG. 2, the rail or lip 102r may have a height H. As shown in FIG. 2, the rail 101r may be disposed at the distal end of the shelf 101 at the widest point of the shelf 101. However, the rail 101r may also extend around the sides of the shelf 101. The shelf 101 may further include a mounting surface 101a, which may be a vertical edge or surface which may be 2 inches in length, and may be disposed a proximal end of the shelf 101 and secured to the wall W via a fastener S, such as a screw, a nail, or a bolt, for example.

The shelf 101 may include a motion detector 40 disposed at or near the rail or lip 101r such that the motion detector 40 may detect the presence of individuals near the shelf 101 such that the light sources 102 may be de-energized or turned off, thereby inhibiting the potential for an individual to be exposed to harmful UV light. As shown in FIG. 2, the motion detector 40 may be disposed at or near the angle 103.

In addition, the motion detector and the light strips 104, 106 may be operatively coupled to a programmed controller 42, which controls the times and duration that the light strips 104, 106 are in an energized condition according to certain events. For example, the detection of the presence of an individual as sensed by the motion detector 40 may cause the de-energization or turning off of the light source 102, thereby minimizing harmful exposure to the UV light.

Figure 3:
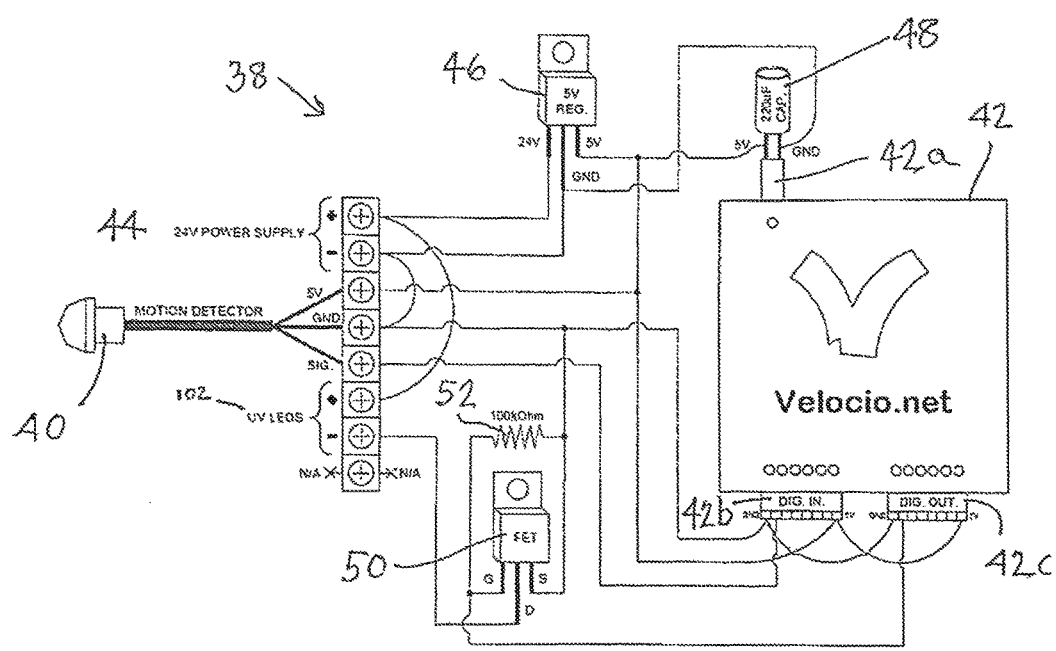
FIG. 3 is a schematic of a circuit diagram in accordance with the present disclosure.

Any programmed controller can be used to provide these functions. As shown in FIG. 3, a circuit 38, by way of example, illustrates the use of a motion detector 40 connected to a programmed controller 42. A power supply 44, such as a 24-volt source, is used to energize the circuit 38, a 5-volt regulator being used, if necessary, to generate a regulated voltage to power the programmed controller 42. A capacitor 48 connected to the controller 42 at port 42a, a field effect transistor (FET) 50 and resistor 52 are connected to input port 42b and output port 42c of the programmed controller as shown. The UV LED light sources 102 are connected as shown, the components connected to the programmed controller 42 enabling the controller 42 to operate as a timer to establish predetermined time intervals, as to be described in connection with FIG. 4. FIG. 3 however, is only one configuration of a programmed controller for timing the operation of the UV-LED's although any other known timers or timing circuits may be utilized for this purpose.

Figure 4:
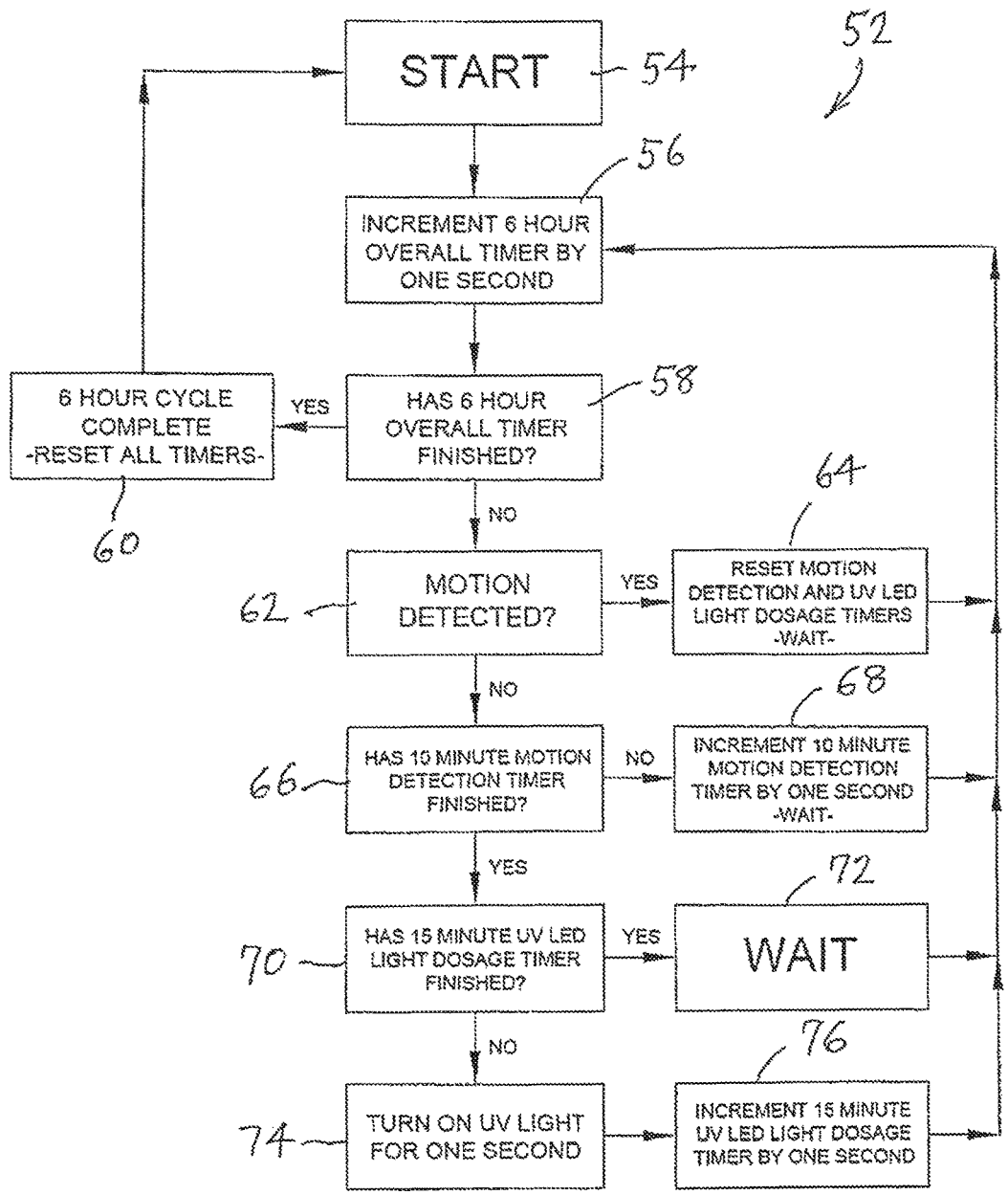
FIG. 4 is a flowchart illustrating an operation of a disinfecting apparatus in accordance with the present disclosure.

Referring to FIG. 4, a flow chart 52 is shown that illustrates the programmed protocol or logic for monitoring and controlling the UV light sources, whether they be LED's, lamps, bulbs, fluorescents, etc. Initially, the controller 42 commences operation at 54 to increment the timer in 6 hour intervals at 56. Thus, without external influences, the controller energizes the UV light sources every 6 hours. The UV light sources are energized four times during each 24-hour period. At 58, the controller 42 queries whether the 6-hour timer has completed its 6 hour interval. After a 6-hour cycle has been completed all the timers are reset at 60 and the controller reverts to the start position at 54. If the 6-hour overall timer has not been completed the controller queries whether the motion detector 40 has detected any motion, at 62. If motion has been detected the motion detection and UV-LED light dosage timers are reset, at 64, and the controller reverts to incrementing the 6-hour overall timer, at 56, to repeat the protocol. If motion has not been detected at 62 the controller queries whether a 10-minute motion detection timer has finished, at 66. If the motion detection timer has not finished the 10-minute motion detection timer is incremented by one second at 68 and the controller reverts to increment 6-hour overall timer at 56. If the 10-minute motion detection timer has finished, at 66, the controller 42 queries whether the 15 minute UV-LED light dosage timer has finished, at 70. If it has finished the controller is instructed to wait, at 72, after which the 6 hour overall hour is incremented by one second, at 56. If the 15 minute UV-LED light dosage timer has not finished, at 70, the UV light sources are turned on for one second, at 74. After the UV light has been activated, at 74, the 15 minute UV-LED timer is incremented by one second, at 76, and the 6-hour overall timer is thereafter incremented again at 56. The cycle is repeated on an ongoing or continuous basis with the program controller 42 regulating the operation or energization of the UV light sources at the preselected or desired time intervals, as may be modified by the presence of individuals sensed by the motion detector 40.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A disinfecting apparatus, comprising:
    a shelf securable to a stationary substantially vertical surface to fix the position of the shelf in a substantially horizontal plane and render it stationary during normal use above a generally unobstructed space below said shelf while exposed to an open surrounding space through which people can move;
    a bracket configured to secure the shelf to the stationary surface;
    an angle remote from said bracket and mounted on said shelf to form a mounting surface inclined relative to said horizontal plane at an angle greater than 0°;
    at least first and second UV light sources coupled to the shelf, said UV light sources being configured to sanitize air and surfaces in proximity to said shelf, said first UV light source directing UV light vertically downwardly into said unobstructed space when said shelf is mounted on the substantially vertical surface and said second UV light source being arranged on said mounting surface to at least partially direct UV light into the open surrounding space through which people can move; and
    a programmable controller being operatively coupled to a motion detector, the controller being programmed to cause at least one of energization and deenergization of the UV light source upon the occurrence of at least one predetermined event and deenergization of the UV light source upon detection of motion within the space in proximity of the shelf independently of the existence of the at least one predetermined event.

2. The disinfecting apparatus of claim 1, wherein said UV light source comprises at least one of an UV LED light, a mercury tube, and a xenon UV tubes.

3. The disinfecting apparatus of claim 1, wherein said source of UV light comprises a plurality of UV-generating LEDs.

4. The disinfecting apparatus of claim 1, wherein said source of UV light generates ultraviolet radiation within the range of 250-290 nm.

5. The disinfecting apparatus of claim 1, wherein said source of UV light generates ultraviolet radiation within the range of 270-280 nm.

6. The disinfecting apparatus of claim 1, further comprising a heat sink to prevent said source of UV light from reaching excessive temperatures.

7. The disinfecting apparatus of claim 1, wherein the UV light source includes a plurality of strips of LEDs.

8. The disinfecting apparatus of claim 1, wherein the strips of LEDs are generally parallel to one another and disposed along a length of the shelf.

9. A disinfecting apparatus, comprising:
- a shelf securable to a stationary substantially vertical surface to fix the position of the shelf in a substantially horizontal plane and render it stationary during normal use above a generally unobstructed space below said shelf while exposed to an open surrounding space through which people can move, said shelf having a lower surface when mounted on the stationary surface;
- a bracket configured to secure the shelf to the surface;
- an angle remote from said bracket and mounted on said shelf to form a mounting surface inclined relative to said horizontal plane at an angle greater than 0°
- at least one UV light source mounted on said lower surface of said shelf and on said mounting surface, the UV light being configured to direct UV light both vertically downwardly and at least partially direct UV light into the open surrounding space through which people can move to sanitize air and surfaces in proximity to said shelf; and
- a controller operatively coupled to a motion detector to cause energization and deenergization of the UV light source upon a predetermined event and deenergization of the UV light source upon detection of motion within the space in proximity of the shelf independently of the existence of a predetermined event.

* * * * *